US005741685A

United States Patent [19]

Vacanti

[11] Patent Number: 5,741,685

[45] Date of Patent: Apr. 21, 1998

[54] PARENCHYMAL CELLS PACKAGED IN IMMUNOPROTECTIVE TISSUE FOR IMPLANTATION

[75] Inventor: Joseph P. Vacanti, Winchester, Mass.

[73] Assignee: Children's Medical Center Corporation, Boston, Mass.

[21] Appl. No.: 473,255

[22] Filed: Jun. 7, 1995

[51] Int. Cl.$^6$ .............................. C12N 11/04; C12N 5/00

[52] U.S. Cl. ......................... 435/182; 424/43.7; 424/422; 435/382; 435/398

[58] Field of Search .................................... 435/174, 177, 435/178, 180, 182, 240.23, 240.22, 382, 395, 396, 398, 402; 424/93.7, 422

[56] References Cited

U.S. PATENT DOCUMENTS

| | | | |
|---|---|---|---|
| 2,609,347 | 9/1952 | Wilson | 521/87 |
| 2,653,917 | 9/1953 | Hammon | 521/136 |
| 2,659,935 | 11/1953 | Hammon | 264/321 |
| 2,664,366 | 12/1953 | Wilson | 15/244.4 |
| 2,664,367 | 12/1953 | Wilson | 15/244.4 |
| 2,846,407 | 8/1958 | Wilson | 521/53 |
| 3,826,241 | 7/1974 | Bucalo | 128/1 R |
| 3,880,991 | 4/1975 | Yollesa | 424/22 |
| 3,883,393 | 5/1975 | Knazek et al. | 435/240 |
| 3,902,497 | 9/1975 | Casey | 128/296 |
| 3,949,073 | 4/1976 | Daniels | 424/177 |
| 3,960,150 | 6/1976 | Hussain et al. | 128/268 |
| 3,974,526 | 8/1976 | Dardik et al. | 3/1.4 |
| 4,026,304 | 5/1977 | Levy | 128/419 F |
| 4,069,307 | 1/1978 | Higuchi et al. | 424/22 |
| 4,137,921 | 2/1979 | Okuzumi | 128/335.5 |
| 4,141,087 | 2/1979 | Shalaby et al. | 3/1 |
| 4,144,126 | 3/1979 | Burbidge | 195/1.1 |
| 4,186,448 | 2/1980 | Brekke | 3/1.9 |
| 4,192,827 | 3/1980 | Mueller et al. | 525/123 |
| 4,205,399 | 6/1980 | Shalaby et al. | 3/1 |
| 4,228,243 | 10/1980 | Iizuka | 435/285 |
| 4,239,664 | 12/1980 | Teng et al. | 260/17.4 |
| 4,243,775 | 1/1981 | Rosensaft et al. | 525/415 |
| 4,277,582 | 7/1981 | Mueller et al. | 525/421 |
| 4,280,954 | 7/1981 | Yannas et al. | 260/123.7 |
| 4,304,591 | 12/1981 | Mueller et al. | 71/93 |
| 4,304,866 | 12/1981 | Green et al. | 435/240.33 |
| 4,347,847 | 9/1982 | Usher | 128/334 |
| 4,348,329 | 9/1982 | Chapman | 260/403 |
| 4,352,883 | 10/1982 | Lim | 435/178 |
| 4,356,261 | 10/1982 | Kuettner | 435/68 |
| 4,391,797 | 7/1983 | Folkman et al. | 424/19 |
| 4,391,909 | 7/1983 | Lim | 435/178 |
| 4,416,986 | 11/1983 | Markus et al. | 435/70.3 |
| 4,431,428 | 2/1984 | Schmer | 604/897 |
| 4,438,198 | 3/1984 | Schmer | 435/178 |
| 4,439,152 | 3/1984 | Small | 433/173 |
| 4,440,921 | 4/1984 | Allcock et al. | 528/168 |
| 4,446,234 | 5/1984 | Russo et al. | 435/29 |
| 4,450,150 | 5/1984 | Sidman | 424/1.1 |
| 4,456,687 | 6/1984 | Green | 435/240 |
| 4,485,096 | 11/1984 | Bell | 424/95 |
| 4,485,097 | 11/1984 | Bell | 424/97 |
| 4,495,174 | 1/1985 | Allcock et al. | 424/78.37 |
| 4,505,266 | 3/1985 | Yannas et al. | 128/1 R |
| 4,520,821 | 6/1985 | Schmidt et al. | 128/334 |
| 4,544,516 | 10/1985 | Hughes et al. | 264/108 |
| 4,545,082 | 10/1985 | Hood | 623/1 |
| 4,546,500 | 10/1985 | Bell | 623/1 |
| 4,553,272 | 11/1985 | Mears | 623/1 |
| 4,563,490 | 1/1986 | Stöl et al. | 524/24 |
| 4,576,608 | 3/1986 | Homsy | 3/1 |
| 4,589,293 | 5/1986 | Goosen et al. | 435/1 |
| 4,609,551 | 9/1986 | Caplan et al. | 424/549 |
| 4,637,931 | 1/1987 | Schmitz | 424/73 |
| 4,642,120 | 2/1987 | Nevo et al. | 623/16 |
| 4,673,566 | 6/1987 | Goosen et al. | 424/19 |
| 4,675,189 | 6/1987 | Kent et al. | 424/90 |
| 4,681,763 | 7/1987 | Nathanson et al. | 424/95 |

(List continued on next page.)

FOREIGN PATENT DOCUMENTS

| | | |
|---|---|---|
| 86116047.7 | 11/1986 | European Pat. Off. . |
| 0282746 | 9/1988 | European Pat. Off. . |
| 0339607 | 11/1989 | European Pat. Off. . |
| 0361957 | 4/1990 | European Pat. Off. . |
| 62011459 | 1/1987 | Japan . |
| 63-074498 | 4/1988 | Japan . |
| 63196273 | 8/1988 | Japan . |
| 63196595 | 8/1988 | Japan . |
| PCT/US8700869 | 4/1987 | WIPO . |
| WO 87/06120 | 10/1987 | WIPO . |
| PCT/7288/02447 | 7/1988 | WIPO . |
| WO 89/00413 | 1/1989 | WIPO . |
| WO 91/01720 | 2/1991 | WIPO . |
| WO 92/06702 | 4/1992 | WIPO . |
| 9219195 | 11/1992 | WIPO . |
| WO 94/21299 | 9/1994 | WIPO . |

OTHER PUBLICATIONS

Alberts et al., *Molecular Biology of the Cell*, 893 and 894 (1983).

(List continued on next page.)

*Primary Examiner*—David M. Naff
*Attorney, Agent, or Firm*—Arnall Golden & Gregory, LLP

[57] ABSTRACT

Cells for implantation into a patient are packaged within a barrier of immunoprotective tissue prior to implantation to obviate or minimize rejection of the cells. The preferred immunoprotective tissue for forming the barrier is cartilage. The tissue is formed into a layer that is thin enough to allow diffusion of nutrients and gases into the center of a cell mass packaged within the immunoprotective tissue. Typically the layer is less than 300 microns, preferably between 5 and 20 microns. Cells to be implanted, typically dissociated parenchymal cells including hepatocytes, Islets of Langerhans, or other cells having metabolic functions, are then placed on the tissue layer, and the layer is folded to seal the cells to be implanted within the tissue layer. In the preferred embodiment, the dissociated cells are first seeded onto a polymeric fiber matrix. The packaged cells are then implanted at a location providing an appropriate blood supply for diffusion of nutrients and gases through the tissue layer, for example, adjacent the mesentery. Islets of Langerhans are packaged within a tissue layer formed by a monolayer of chondrocytes seeded onto polymer fibers.

10 Claims, 2 Drawing Sheets

U.S. PATENT DOCUMENTS

| | | | |
|---|---|---|---|
| 4,713,070 | 12/1987 | Mano | 623/1 |
| 4,721,096 | 1/1988 | Naughton et al. | 128/1 R |
| 4,757,017 | 7/1988 | Cheung | 435/240.33 |
| 4,757,128 | 7/1988 | Domb | 528/271 |
| 4,778,749 | 10/1988 | Vasington et al. | 435/2 |
| 4,803,168 | 2/1989 | Jarvis, Jr. | 435/240 |
| 4,806,355 | 2/1989 | Goosen et al. | 424/424 |
| 4,846,835 | 7/1989 | Grande | 623/11 |
| 4,853,324 | 8/1989 | Viles | 435/2 |
| 4,868,121 | 9/1989 | Scharp et al. | 435/268 |
| 4,880,622 | 11/1989 | Allcock et al. | 514/772.3 |
| 4,891,225 | 1/1990 | Langer et al. | 424/428 |
| 4,946,938 | 8/1990 | Magill | 528/399 |
| 4,963,489 | 10/1990 | Naughton et al. | 435/240.1 |
| 4,988,761 | 1/1991 | Ikada et al. | 524/557 |
| 5,032,508 | 7/1991 | Naughton et al. | 435/32 |
| 5,041,138 | 8/1991 | Vacanti et al. | 623/16 |
| 5,324,518 | 6/1994 | Orth et al. | 424/423 |
| 5,514,378 | 5/1996 | Mikos et al. | 424/425 |

OTHER PUBLICATIONS

Allcock, et al., "Synthesis of Poly(amino acid alkyl ester) phosphazenes," *Macromolecules*, 10:824–830 (1977).

Allcock, H.R., et al., "Phosphonitrilic Compounds. XV. High Molecular Weight Poly[bis(amino)phosphazenes] and Mixed–Substituent Poly(aminophospazenes)," *Inorg. Chem.*, 11(11), 2584–2590 (1972).

Atala, A., et al., "Endoscopic Treatment of Reflux with Autologous Bladder Muscle Cells," American Academy of Pediatrics meeting held in Dallas, Texas on Oct. 23, 1994, Abstract.

Leeson, et al., Histology W. B. Saurdins Co. pp. 86, 87, 114 (1976).

Lim, et al., J. Pharm. Sci70(4):351–354 (1981).

Pitman, M., et al., "The Use of Adhesives in Chondrocyte Transplantation Surgery: In–Vivo Studies," *Bulletin of the Hospital for Joint Diseases Orthopaedic Institute*, 49(2):213–220 (1989).

Thuroff, et al. Urology 21(2):155–157 (1983).

Upton, J., Plastic and Reconstructive Surgery 68(2):166–174 (1981).

Upton, J., *Plastic and Reconstructive Surgery* 68(2):166–174 (1981).

Urbinska, et al, Exp. Eye Res. 24(3):241–247 (1977).

Vacanti, et al., Journal of Pediatric Surgery 23(1):3–9 (1988).

Vacanti, et al., *Plastic and Reconstructive Surgery*88(5):753–759 (Nov. 1991).

Vacanti, et al., *Nat. Res. Soc. Symp. Proc.* 252:367–373 (1992).

Wozney, J., *Science* 242:1528–1534 (Dec. 16, 1988).

Allcock, et al., "Synthesis of Sugar–Substituted Cyclic and Polymeric Phosphazenes and Their Oxidation, Reduction, and Acetylation Reactions," *Macromolecules*, 16(4):715 (1983).

Allcock, et al., "Polyphosphazenes with Etheric Side Groups: Prospective Biomedical and Solid Electrolyte Polymers," *Macromolecules*, 19(1):1508 (1986).

Allcock, et al., "Amphiphilic polyphosphazenes as membrane materials: influenece of side group on radiation cross–linking," *Biomaterials*, 9(6):500–508 (1988).

Allcock, et al., "Glyceryl Polyphosphazenes: Synthesis, Properties, and Hydrolysis," *Macromolecules*, 21(7):1980–1985 (1988).

Allcock, et al., "Hydrolysis Pathways for Aminophosphazenes," *Inorg. Chem.*, 21(1):515–521 (1982).

Allcock, et al., "An Ionically Cross–Linkable Polyphosphazene: Poly[bis(carboxylatophenoxy)phosphazene] and Its Hydrogels and Membranes," *Macromolecules*, 22(1):75 (1989).

Anderson, David J., et al., *Caltech Biology*, (1987).

Anderson, Kathryn D., et al., "Gene Expression in Implanted Rat Hepatocytes Following Retroviral–Mediated Gene Transfer," *Somatic Cell and Molecular Genetics*, 15:215–227 (1989).

Backlund, Erik–Olof, et al., "Toward a Transplantation Therapy in Parkinson's Disease," *Annals of the N.Y. Academy of Science*, 495:658–673 (1987).

Ben–Ze'ev, A., et al., "Cell–Cell and Cell–Matrix Interactions Differentially Regulate the Espression of Hepatic and Cytoskeletal Genes in Primary Cultures of Rat Hepatocytes," *Proc. Natl. Acad. Sci, USA*, 85:2161–2165 (1988).

Berrino, Pietro, et al., "Surgical Correction of Breast Deformities Following Long–Lasting Complications of Polyurethane–Covered Implants," *Ann. Plast. Surg.*, 24:481 (1990).

Biers, Elizabeth, "Organogensis' Human Artery Equivalent May Revolutionize Vascular Grafts," *Genetic Engineering News*, (1987).

Bissell, D. Montgomery, et al., "Interactions of Rat Hepatocytes with Type IV Collagen, Fibronectin and Laminin Matrices, Distinct Matrix–Controlled Modes of Attachment and Spreading," *European Journal of Cell Biology*, 40:72–78 (1986).

Bissell, D.M., et al., "Support of Cultured Hepatocytes by a Laminin–Rich Gel, Evidence of a Functionally Significant Subendothelial Matrix in Normal Rat Liver," *J. Clin. Invest.*, 79:801–812 (1987).

Bissell, D.M., et al., "The Role of Extracellular Matrix in Normal Liver," *Scand. J. Gastroenterol*, 23:107 (1988).

Björklund, A., *Annals of the N.Y. Academy of Science*, 495:676–686 (1987).

Bohn, M.C., et al., "Advanced Medulla Grafts Enhance Recovery of Striatal Dopaminergic Fibers," *Science*, 238(4817):913–6 (1987).

"Brain Graft Seeks to Relieve Huntington Disease Patient," *The New York Times* (1988).

Brown, Norman, "Fibrin–Collagen Nerve Repair Device," Inventors: Russ Griffiths, Larry Stensaas and Ken Horch, Letter dated May 10, 1988.

Children's Hospital (The), Department of Nursing, Division 5, "Liver Transplantation," (1984).

Chuang, Vincent P., et al., "Sheath Needle for Liver Biopsy in High–Risk Patients," *RSNA*, 261–262 (1988).

Collier, T.J., et al., "Norepinephrine Deficiency and Behavorial Senescence in Aged Rats: Transplanted Locus Ceruleus Neurons as an Experimental Replacement Therapy," *Annals of the New York Academy of Sciences*, 495:396–403 (1987).

*Concise Encyclopedia of Polymer Science*, and Engineering, J. Kroschwitz, ed. (John Wiley & Sons New York 1990).

Craig, et al., "A Biologic Comparison of Polyglactin 910 and Polyglycolic Acid Synthetic Absorbable Sutures," *Surgery Gynecology & Obstetrics*, 141(1):1–10 (1975).

Culliton, Barbara J., "Gore Tex Organoids and Genetic Drugs," *Science*, 246:747–749 (1989).

Davis, George E., et al., "Human Amnion Membrane Serves as a Substratum for Growing Axons In Vitro and In Vivo," *Science*, 236:1106–1109 (1987).

da Silva, C.F., et al., "An In Vivo Model to Quantify Motor and Sensory Peripheral Nerve Regeneration Using Bioresorbable Nerve Guide Tubes," *Brain Research*, 342:307–315 (1985).

del Cerro, M., et al., "Retinal Transplants into the Anterior Chamber of the Rat Eye," *Neuroscience*, 21(3):707–23 (1987).

Doillon, C.J., et al., "Collagen–Based Wound Dressings: Control of the Pore Structure and Morphology," *Journal of Biomedical Materials Research*, 20:1219–1228 (1986).

Doillon, C.J., et al., "Epidermal Cells Cultured on a Collagen–Based Material," G.W. Bailey, Editor, *Proceedings of the 44th Annual Meeting of the Electron Microscopy Society of America*, (1986).

Folkman, Judah, et al., "Angiogenic Factors," *Science*, 235:442–447 (1987).

Fontaine, H., et al., "Optimization Studies on Retroviral Mediated Gene Transfer into Rat Hepatocytes: Implications for Gene Therapy," The Society of University Surgeons, Resident's Program, Cincinnati, Ohio (1992).

Gash, D.M., et al., "Amitotic Neuroblastoma Cells Used for Neural Implants in Monkeys," *Science*, 233(4771):1420–2 (1986).

Gash, D.M., "Neural Transplantation: Potential Therapy for Alzheimer's Disease," *J. Neural Transm.*, [Suppl.] 24:301–8 (1987).

E. Goethals, editor, *Polymeric Amines and Ammonium Salts* (Pargamen Press, Elmsford, N.Y. 1980).

Grande, Daniel A., et al., "Healing of Experimentally Produced Lesions in Articular Cartilage Following Chondrocyte Transplantation," *The Anatomical Record*, 218:142–148 (1987).

Grande, Daniel A., et al., "The Repair of Experimentally Produced Defects in Rabbit Articular Cartilage by Autologous Chondrocyte Transplantation," (1988).

Grolleman, et al., *J. Controlled Release*, 3:143 (1986).

Harris, A.K., et al., "Silicone Rubber Substrata: A New Wrinkle in the Study of Cell Locomotion," *Science* (Wash, D.C.), 208:177–179 (1980).

Henry, E.W., et al., "Nerve Regeneration Through Biodegradable Polyester Tubes," *Exp. Neurol.*, 90(3):652–76 (1985).

Ingber, D.E., et al., "Cells as Tensegrity Structures: Architectural Regulation of Histodifferentiation by Physical Forces Transduced Over Basement Membrane," *Gene Expression During Normal and Malignant Differation*, L.C. Andersson, et al., 13–32 (Academic Press, Orlando, FL. 1985).

Ingber, et al., "Endothelial Growth Factors and Extracellular Matrix Regulate DNA Synthesis Through Modulation of Cell and Nuclear Expansion," *In Vivo Cellular & Developmental Biology*, 23(5):387–394 (1987).

Ingber, et al., "Control of Capillary Morphogenesis: A Molecular System of Mechanical Switches," *J. Cell Biol.*, 107:797a (1988).

Ingber, et al., "Growth Control through Fibronectin–Dependent Modulation of Cell Shape," *J. Cell Biol.*, 105:219a (1987).

Ingber, et al., "How Does Extracelluar Matrix Control Capillary Morphogenesis?", *Cell*, 58:803–805 (1989).

Ingber, et al., "Mechanochemical Switching Between Growth and Differentiation During Fibroblast Growth Factor–Stimulated Angiogenesis Vitro: Role of Extracellualr Matrix," *J. Cell Biol.*, 109:317–330 (1989).

Jauregui, H.O., et al., "Attachment and Long Term Survival of Adult Rat Hepatocytes in Primary Monolayer Cultures: Comparison of Different Substrata and Tissue Culture Media Formulations," *In Vitro Cellular & Development Biology*, 22(1):13–22 (1986).

Kleinman, H.K., et al., "Use of Extracellular Matrix Components for Cell Culture," *Analytical Biochemistry*, 166:1–13 (1987).

Kolata, Gina, "Parkinson Procedure: Fervor Turns to Disillusion," *The New York Times*, (1988).

Kordower, J.H., et al., "An in Vivo and in Vitro Assessment of Differentiated Neuroblastoma Cells as a Source of Donor Tissue for Transplantation," *Annals of the New York Academy of Sciences*, 495:606–622 (1987).

Kordower, J.H., et al., "Neuroblastoma Cells in Neural Transplants: A Neuroanatomical and Behavioral Analysis," *Brain Research*, 417(1):85–98 (1987).

Kusano, et al., *Acta Japoni Hepato*, 63:345–351 (Asahikawa, Japan 1989).

Leong, K.W., et al., "Bioerodible Polyanhydrides as Drug–carriers Matrices, I; Characterization, Degradation, and Release Characteristics," *Journal of Biomedical materials Research*, 19:941–955 (1985).

Letourneau, "Possible Roles for Cell–to–Substratum Adhesion in Neuronal Morphogenesis," *Developmental Biology*, 44:77–91 (1975).

Lewin, "Cloud over Parkinson's Therapy," *Science*, 240:390–392, (1988).

Lewin, "Disappointing Brain Graft Results," *Science*, 1407 (1988).

Li, M.L., et al., "Influence of a Reconstituted Basement Membrane and Its Components on Casein Genes Expression and Secretion in Mouse Mammary Epithelial Cells," *Proc. Natl. Acad. Sci. USA*, 84:136–140 (1987).

Macklis, J.D., et al., "Cross–Linked Collagen Surface for Cell Culture that is Stable, Uniform, and Optically Superior to Conventional Surfaces," *In Vitro Cellular & Developmental Biology*, 21:(3) part I, 189–194 (1985).

Madison, R., et al., "Increased Rate of Peripheral Nerve Regeneration Using Bioresorbable Nerve Guides and a Laminin–Containing Gel," *Exp. Neurol.*, 88(3):767–72 (1985).

Madison, R., et al., "Nontoxic Nerve Guide Tubes Support Neovascular Growth in Transected Rat Optic Nerve," *Exp Neurol.*, 86(3):448–61 (1984).

Madison, R., et al., "Peripheral Nerve Regeneration With Entubulation Repair: Comparison of Biodegradeable Nerve Guides Versus Polyethylene Tubes and the Effects of a Laminin–Containing Gel," *Exp Neurol.*, 95(2):387–90 (1987).

Marciano, F.F., et al., "Structural and Functional Relationships of Grafted Vasopressin Neurons," *Brain Res.*, 370(2):338–42 (1986).

Mesnil, et al., "Cell Contact but Not Junctional Communication (Dye Coupling) with Biliary Epithelial Cells is Required for Hepatocytes to Maintain Differentiated Functions," *Exper. Cell Res.*, 173:524–533 (1987).

Michalopoulos, G., et al., "Primary Culture of Parenchymal Liver cells on Collagen Membranes," *Exper. Cell. Res.*, 94:70–78 (1975).

Millaruelo, Ana I., "Role of Plasminogen Activator and its Inhibitors in Axonal Outgrowth and Regeneration In Vivo," *Caltech Biology* (1987).

Mooney, David, et al., "Control of Hepatocyte Function Through Polymer–Substrate Modulation," Thesis Proposal—Department of Chemical Engineering, Massachusetts Institute of Technology (1989).

Mooney, David, et al., "Switching from Differentiation to Growth in Hepatocytes by Extracellular Matrix," *J. Cell Biology*, 111(5):149a (1990).

Movitz, David, "Accessory Spleens and Experimental Splenosis Principles of Growth," *The Chicago Medical School Quarterly*, 26(4):183–187 (1967).

Nastelin, Jennifer Green, "Pancreatic Islet Cell Transplantation: Optimization of Islet Cell Adhesion by Altering Polymer–Surface Characteristcs," Harvard–M.I.T. Division of Health Sciences and Technology (1990).

Naughton, B.A., et al., "Granulopoiesis and Colony Stimulating Factor Production in Regenerating Liver," *Exp. Hematol.*, 10(5):451–458 (1982).

Naughton, B.A., et al., "Long–Term Growth of Rat Bone Marrow Cells in a Three–Dimensional Matrix," *The Anatomical Record*, 18(1):97A (1987).

Naughton, G.K., et al., "Erythropoietin Production by Macrophages in the Regenerating Liver," *Journal of Surgical Oncology*, 30:184–197 (1985).

Notter, M.F., et al., "Neuronal Properties of Monkey Adrenal Medulla in Vitro," *Cell Tissue Res.*, 244(1):69–76 (1986).

Nvilas E., et al., "Peripheral Nerve Repair with Bioresorbable Prosthesis," *Trans. Am. Soc. Artif. Intern. Organs*, 29:307–13 (1983).

Oellrich, R.G., et al., "Biliary Atresia," *Neonatal Network*, 25–30 (1987).

Oliwenstein, Lori, "The Power of Plastics," *Discover*, 18 (1989).

Omery, Anna, et al., "A Nursing Perspective of the Ethical Issues Surrounding Liver Transplantation," *Heart & Lung*, 17(6) (1988).

Pasik, P., *Annals of the N.Y. Academy of Science*, 495:674–675 (1987).

Patterson, P.H., et al., "Adrenal Chromaffin Cell–Derived Cholinergic Neurons for Brain Transplants," *Caltech Biology* (1987).

Patterson, P.H., et al., *Caltech Biology*, 199–200 (1987).

Perlow, M.J., "Brain Grafting as a Treatment for Parkinson's Disease," *Neurosurgery*, 20(2), 335–342 (1987).

Pimpl, et al., "Experimental Studie zur Frage der Transplantatkonditionierung and Transplantatgröfe Bei Heterotoper Autologer Milztransplantation," *Lagenbecks Archiv.*, 37215–36218 (1984).

Pimpl, et al., "Perfusion of Autologous Splenic Grafts Correlation with Specific Immunological Functions: An Experimental Study in Pigs," *Eur. Surg. Res.*, 19:53–61 (1987).

Ptasinska–Urbanska, et al., "Intrascleral Introduction of Isolated Allogeneic Chondrocytes Capable of Cartilage Reformation in Rabbits; Possible Procedure in Treatment of Detachment of the Retina," *Exp. Eye Res.*, 24(3):241–247 (1977).

Redmond, D.E., Jr., et al., "Fetal Neuronal Grafts in Monkeys Given Methyphenyltetrahydropyridine," *The Lancet*, 1125–1127 (1986).

Redmond, D.E., Jr., et al., "Transplants of Primate Neurons," *Lancet*, 2(8514):1046 (1986).

Reid, L.M., et al., "Long–Term Cultures of Normal Ray Hepatocytes on Liver Biomatrix," *Ann. NY Acad. Sci.* (1980).

Rhine, et al., "Polymers for Sustained Macromolecule Release: Procedures to Fabricate Reproducible Delivery Systems and Control Release Kinetics," *Journal of Pharmaceutical Sciences*, 69(3) (1980).

Rosen, Howard B., et al., "Bioerodible Polymers for Controlled Release Systems," *Controlled Release Systems: Fabrication Technology*, 11(5):83–110 (1983).

Rosen, Howard B., et al., "Bioerodible Polyanhydrides for Controlled Drug Delivery," Butterworth & Co. (Publishers) Ltd. (1983).

Sapoznikova, et al., "Morphological Changes in Splenic Autografts Following Splenectomy: Experimental and Clinical Findings," *Biological Abstracts*, 86:76896 (1987): *Arkhiv Patologii*, 49(12):31–37 (1987).

Sasaki, K., "Neovascularization in the Splenic Autograft Transplanted into Rat Omentum as Studied by Scanning Electron Microscopy of Vascular Casts," *Virchows Arch. [Pathol. Anat.]*, 409:325–334 (1986).

Sawada, N., et al., "Effects of Extracellular Matrix Components of the Growth and Differentiation of Cultured Rat Hepatocytes," *In Vitro Cellular & Developmental Biology*, 23(4):267–273 (1987).

Schmeck, Harold M., "Doctors Try to Capitalize on the Liver's Ability to Regenerate Itself,"*The New York Times Medical Science* (1989).

Seckel, B.R., et al., "Nerve Regeneration Through Synthetic Biodegradable Nerve Guides: Regulation by the Target Organ," *Plast. Reconstr. Surg.*, 74(2):173–81 (1974).

Shine, H.D., et al., "Cultural Peripheral Nervous System Cells Support Peripheral Nerve Regeneration Through Tubes in the Absence of Distal Nerve Stump," *J. Neuroscience Res.*, (14):393–401 (1985).

Siegel, Ronald A., et al., "Controlled Release of Polypeptides and Other Macromolecules," *Pharmaceutical Research*, 2–10 (1984).

Sirica, Alphonse, et al., "Fetal Phenotypic Expression by Adult Rat Hepatocyctes on Collagen Gel/Nylon Meshes," *Proc. National Academy Science USA*, 76(1):283–287 (1979).

Sirica, Alphonse, et al., "Use of Primary Cultures of Adult Rat Hepatocytes on Collagen Gel–Nylon Mesh to Evaluate Carcinogen–Induced Unscheduled DNA Synthesis," *Cancer Research*, 40:3259–3267 (1980).

Sladek, J.R., Jr., et al., "Reversal of Parkinsonism by Fetal Nerve Cell Transplants in Primate Brain," *Annals of the New York Academy of Sciences*, 495:641–657 (1987).

Sladek, J.R., Jr., et al., "Survival and Growth of Fetal Catecholamine Neurons Transplanted into Primate Brain," *Brain Res. Bull.*, 17(6):809–18 (1986).

Sladek, John R., Jr., et al., "Neural Transplantation: A Call for Patience Rather Than Patients," *Science*, 240:386–388 (1988).

Sladek, John R., Jr., et al., "Transplantation of Fetal Dopamine Neurons in Primate Brain Reverses MPTP Induced Parkinsonism," *Progress in Brain Research*, 71:309–323 (1987).

Stemple, Derek L., "A Factor that Induces Adrenergic Differentation in Avian Neural Crest Cells," *Caltech Biology*, (1987).

Sudhakaran, P.R., et al., "Modulation of Protein Synthesis and Secretion by Substratum in Primary Cultures of Ray Hepatocytes," *Exper. Cell Res.*, 167:505–516 (1986).

Sullivan, Walter, "Spinal Injury Research Yields a Glimmer of Hope," *The New York Times* (1987).

Tayassoli, Mehdi, et al., "Studies on Regeneration of Heterotopic Splenic Autotransplants," *Blood*, 41(5):701–709 (1973).

Thompson, John A., et al., "Heparin–Binding Growth Factor 1 Induces the Formation of Organoid Neovascular Structures In Vivo," *Proc. Natl. Acad. Sci. U.S.A.*, 86:7928–7932 (1989).

Thompson, J.A., et al., "Implantable Bioreactors: Modern Concepts of Gene Therapy," *Current Communications in Molecular Biology: Therapeutic Peptides and Proteins*, D. Marshak, ed., 143–147 (1989).

Tomomura, Akito, et al., "The Control of DNA Synthesis in Primary Cultures of Hepatocytes From Adult and Young Rats: Interactions of Extracellular Matrix Components, Epidermal Growth Factor, and the Cell Cycle," *J. Cellular Physiology*, 130(1):221–227 (1987).

Unipoint Industires, Inc., "Polyvinyl Alcohol Foam for Surgical and Industrial Use" (May 1983).

UNOS Update, "National Cooperative Transplantation Study Completed," 7(10) (1991).

Vacenti, Joseph P., "Beyond Transplantation," *Arch. Surgery*, 123:545–549 (1988).

Vargo, Rita, et al., "Infection as a Complication of Liver Transplant," *Critical Care Nurse*, 9(4):52–62.

Viig, J., et al., "UV–Induced DNA Excision Repair in Rat Fibroblasts During Immortalization and Terminal Differentiation In Vitro," *Exp. Cell Res.*, 167:517–530 (1986).

Yannas, I.V., et al., "Artificial Skin: A Fifth Route to Organ Repair and Replacement," *Iss. Polym. Biomaterial*, 106:221–230 (1986).

Yannas, I.V., et al., "Polymeric Template Facilitates Regeneration of Sciatic Nerve Across 15MM," *Polym. Material Sci. Eng.*, 53:216–218 (1985).

Yannas, I.V., "Wound Tissue Can Utilize a Polymeric Template to Synthesize a Functional Extension of Skin," *Science*, 215:174–176 (1982).

Hans–Lukas Teuber Symposium at Massachusetts Institute of Technology, "The Biological Basis of Brain Transplants" Apr. 12, 1988.

Symposium at Massachusetts Institute of Technology, "Tissue Transplantation on the Treatment of Parkinson's Disease", Apr. 13, 1988.

Atala, et al., "Injectable Alginate Seeded with Chondrocytes as a Potential Treatment for Vesicoureteral Reflux", *Journal of Urology*, vol. 150, No. 2, part 2, 745–747 (Aug. 1993).

Paige, et al., Abstract "De Novo Cartilage Generation Utilizing Calcium Alginate–Chondrocyte Constructs" 1993 Plastic Surgery Research Council Meeting, Houston, TX (Apr. 28–May 1, 1993).

Abstract "Injectable Alginate Seeded with Chondrocytes as a Potential Treatment for Vesicoureteral Reflux", Annual Meeting of the Section on Urology, American Academy of Pediatrics Oct. 10–15, 1992.

12
10
10
12

PARENCHYMAL CELLS PACKAGED IN IMMUNOPROTECTIVE TISSUE FOR IMPLANTATION

BACKGROUND OF THE INVENTION

The present invention generally relates to a method and composition for minimizing rejection of foreign cells implanted into an individual in need thereof, and more specifically is directed to a method using a barrier formed of immunoprivileged cells around the cells to be implanted.

A variety of methods have been used to prevent rejection of foreign cells, either allografts or xenografts, following implantation into an individual having a competent immune system. In most cases of organ transplantation, it is not possible to obtain autografts, so allografts are used in combination with immunosuppression using a drug such as cyclosporin. Cyclosporin is expensive, must be used daily for the rest of the life of the patient, and has side effects which can be serious. Autografts are typically possible only in the case of cells forming cartilage and skin. Other methods that have been used to prevent rejection of foreign cells have typically used synthetic materials such as alginate or polylysine-polyethylene glycol polymers that can be ionically crosslinked to form microcapsules that can be implanted to protect the cells, but still allow diffusion of nutrients and gases into and out of the microcapsules, along with the soluble products of the implanted cells. These materials tend to biodegrade after a period of time, however, and the cells are destroyed. Attempts to overcome this problem using non-biodegradable synthetic polymers such as ethylene vinyl acetate or polymethacrylate have been equally limited in effectiveness due to encapsulation of the implanted material by fibrotic material which "walls off" the foreign material from the rest of the tissues.

For example, Diabetes Mellitus is a common disorder of the glucose metabolism due to a reduction of insulin production or secretion. Six percent of the U.S. population (14 million patients) suffer from this disease; four million are on regular insulin medication. There are 30,000 new cases of Insulin Dependent Diabetes Mellitus (IDDM) every year. The estimated annual health care costs and lost wages are $92 billion. Diabetes Mellitus is the third most common disease and the eighth leading cause of death in the US. The standard therapy for patients with IDDM is a subcutaneous administration of insulin, a polypeptide, in differently intense regimens. Since this method of therapy does not provide the natural glucose/insulin feedback mechanism, frequent blood glucose measurements to adjust the dose of insulin are necessary. Events of glucose imbalance are still threatening and chronic complications will still occur.

Some current experimental therapeutic approaches try to overcome those problems by transplanting Islets of Langerhans. The β-cells of the islets produce and secrete the insulin and control the glucose/insulin feedback. Clinically the Islets of Langerhans are transplanted by transplantation of the entire pancreas although they represent only 1 to 2% of the pancreas mass or by transplantation of isolated islets. The two major problems are the necessity of immunosuppression and the scarcity of donor tissue, as discussed above.

Other methods for addressing the problem with rejection include immunomodulation, where the cell surface is altered so that the immune system can not recognize those cells as foreign, and immunoprotection, where a barrier for immunorecognition of the transplanted cells/tissue is provided, as discussed above. Current attempts utilize gelatinous or membranous inert materials to encapsulate the islets. Major problems of those methods have been that either the passage of nutrients for the islets was not sufficient or the materials attracted a non-specific immununoresponse against the cells.

It is therefore an object of the present invention to provide a method and compositions for implanting allografts and xenografts into a patient which minimizes the need for immunosuppression or subsequent rejection of the cells.

SUMMARY OF THE INVENTION

Cells for implantation into a patient in need thereof are packaged within an immunoprotective barrier prior to implantation, thereby obviating or minimizing rejection of the cells. The preferred immunoprivileged tissue for forming the barrier is cartilage, although other tissues include cells forming the blood brain barrier as well as other cell types. The tissue is formed into a layer that is thin enough to allow diffusion of nutrients and gases into the center of the cell mass placed within the immunoprotective barrier, typically less than 300 microns, preferably between 5 and 20 microns. In the preferred embodiment, the barrier is formed by culturing dissociated cells directly on the surface of a culture dish or on a polymeric matrix, for example, formed of polyglycolic acid suture fibers spread on the bottom of a culture dish. Cells are grown to confluence, and in the case of chondrocytes, until matrix has been deposited. Cells to be implanted, typically dissociated parenchymal cells including hepatocytes, Islets of Langerhans, or other cells having metabolic functions, are then placed on the barrier, and the barrier folded to seal the cells to be implanted within the barrier. In the preferred embodiment, the dissociated cells are first seeded onto a polymeric fiber matrix. The packaged cells are then implanted at a location providing an appropriate blood supply for diffusion of nutrients and gases through the barrier, for example, adjacent the mesentery.

The example demonstrates encapsulation of Islets of Langerhans within a barrier formed by a monolayer of chondrocytes seeded onto polymer fibers.

DETAILED DESCRIPTION OF THE INVENTION

A. Immunoprotective Barrier

Immunoprivileged Tissue

Figure 1:
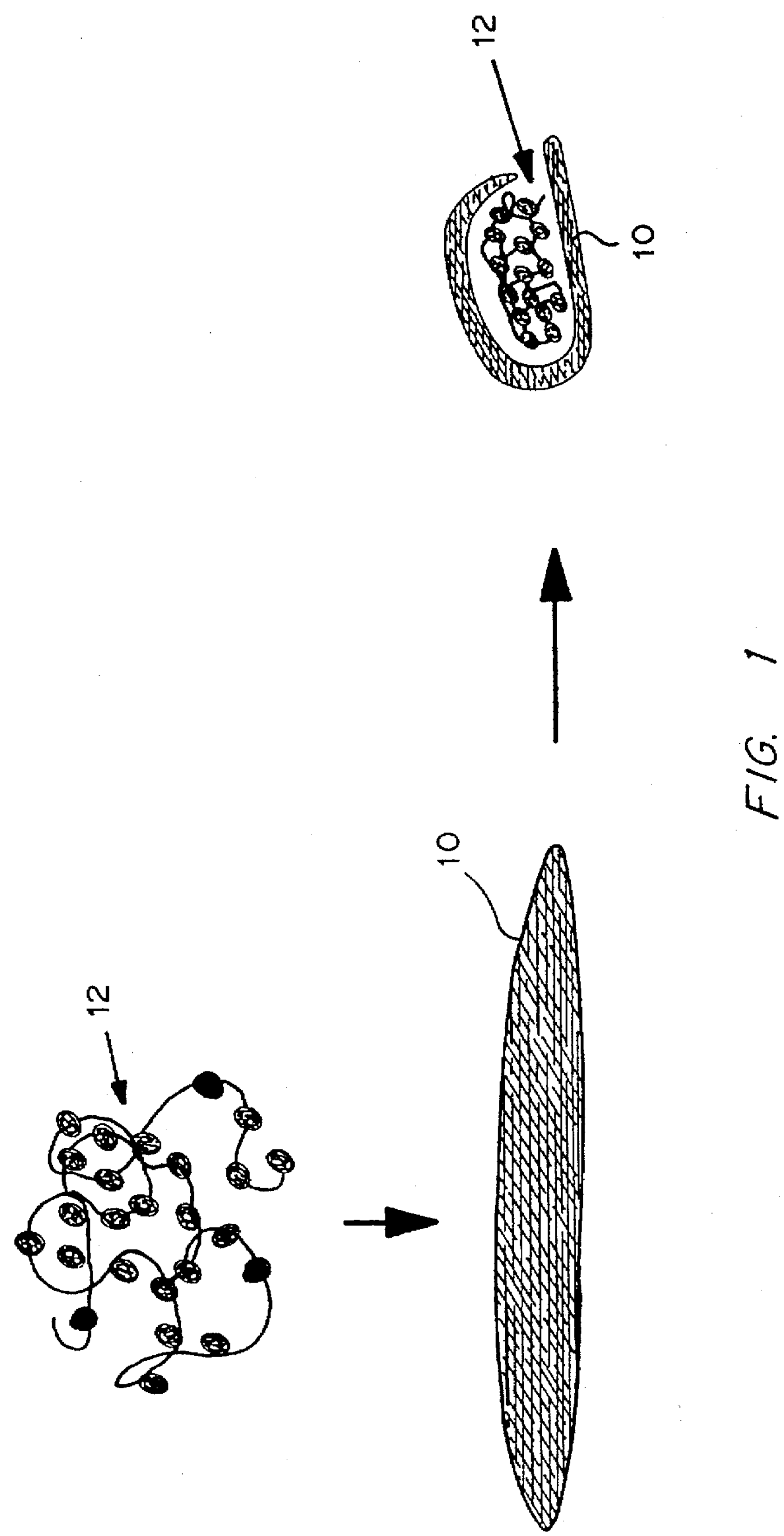
FIG. 1 is a schematic of the packaging of dissociated parenchymal cells attached to a polymeric fiber matrix within a monolayer of cartilage formed by chondrocytes proliferated on a fiber matrix.

Immunoprivileged tissue refers to tissues that surround a region of the body which is not exposed to a immune response. Examples include cartilage, the interior of the eye containing the vitreous, the vascular endothelium of the brain (the blood brain barrier), the maternal-fetal interface in the placenta, and the region of the testicles isolating the sperm. In the preferred embodiment described herein, cells forming cartilage such as chondrocytes or fibroblasts are used to form an immunoprotective barrier.

Cells are typically obtained by biopsy, most preferably from the patient into which the cells are to be implanted, although they can also be obtained from established cells lines or related individuals. Cells are obtained using standard techniques, for example, by punch biopsy or laproscopic surgery. Cells are dissociated by treatment using collagenase or trypsin, using standard methodology.

Matrix

Although it is not essential to seed the cells onto a matrix for use in forming an immunoprotective barrier, a matrix can be used to provide structural support for the cells to facilitate transfer and packaging of the cells to be implanted. Examples of suitable matrix materials are biodegradable or non-biodegradable polymers including polyhydroxy acids such as polyglycolic acid, polylactic acid, and copolymers thereof, polyanhydrides, polyorthoesters, polymers of synthetic and natural proteins, ethylene vinyl acetate, polyvinyl alcohol and many other polymers suitable for implantation into a person. The polymer is preferably in fibrous form, which can range from a single fiber of the type used as a suture, typically coiled or intertwined to form a support structure on a single plane, to woven or non-woven matrices of fibers, to porous sponge-like matrices.

Method for Manufacture

The dissociated cells of the immunoprivileged tissue are seeded onto the fibrous matrix, or seeded onto the bottom of a culture dish, and grown under standard conditions to confluence. Chondrocytes or fibroblasts are preferably grown until matrix is deposited and the tissue has the histology of cartilage. The cells are preferably in a very thin layer, ranging from a monolayer of cells between 5 and 20 microns in thickness, up to hundreds of microns, depending on the final application. In all cases, the thickness must be sufficient to prevent penetration by immunocompetent cells through the barrier, while allowing sufficient exchange of nutrients and gases and soluble metabolic products for the cells within the barrier to survive and serve their intended purpose.

B. Cells to be Implanted

Although almost any cell can be implanted, the preferred cells are parenchymal cells having a metabolic rather than structural function. Examples include hepatocytes, Islets of Langerhans, spleen, pancreas, gall bladder, kidney, and other tissues having exocrine function. For ease of reference herein, all cells which are to be implanted within the barrier are referred to as "parenchymal cells". The cells are typically obtained from a donor or from cell culture, using standard biopsy or surgical techniques. The cells can also be genetically engineered to produce a desired molecule. Examples include cells engineered to express an enzyme missing or defective in the recipient or which express a therapeutic agent such as a toxin directed against cancer cells. Although discussed herein primarily with reference to allografts and xenografts, the technique can be used to decrease any encapsulation that may be present following implantation of autografts, particular using polymeric matrices that may elicit an inflammatory reaction or as part of the normal inflammatory process associated with surgery.

Cells are dissociated using standard techniques such as incubation in collagenase or trypsin solutions. A sufficient number of cells to provide the desired function following implantation must be obtained. The number of cells required can be determined based on in vitro assays, and known values for certain conditions. For example, many enzymes are measured in the blood stream as indicators of liver function; blood sugar levels are indicative of insulin production. The requisite cell mass for a desired function in a particular patient can also be determined based on comparison with normal organ function.

Packaging within the Barrier

The dissociated parenchymal cells are packaged within the barrier by placing the cells, either directly as obtained from a patient, dissociated, or after cell culture, onto the barrier layer. In the preferred embodiment, the cells are first seeded onto a suitable polymeric matrix, similar to that described above for forming the barrier, having interstitial spacing or pores of between approximately one hundred and 300 microns in diameter, although the structural requirements allow for a more random or thicker three dimensional shape, allowed to attach, and optionally proliferated in cell culture, then placed within the barrier layer. As shown in the following example, the barrier can be folded over the parenchymal cells and allowed to attach to itself, in a manner similar to making of an omelet, to form the final structure for implantation.

C. Implantation

The packaged parenchymal cells are implanted using standard surgical techniques, most preferably immediately adjacent to a highly vascularized tissue such as the mesentery.. Hepatocytes are most preferably implanted with a portocaval shunt, to provide the hepatotrophic factors required for optimal survival of implanted hepatocytes. Implantation into the mesentery is particularly preferred.

The present invention will be further understood by reference to the following non-limiting examples.

EXAMPLE 1

Islet transplantation using a tissue engineered construct of Islets of Langerhans on a polymer scaffold encapsulated with a monolayer of chondrocytes This example utilizes the immunoprotective/immunoprivileged qualities of a chondrocyte matrix. The Islets of Langerhans are encapsulated with chondrocytes of the recipient. The matrix laid down by the chondrocytes protects the islets from immunorecognition of two different kind: first, immunorecognition of the islets as non-autologous (foreign) cells; second, autoimmunorecognition as a part of the disease process (IDDM is thought to be a autoimmune disease). In this way, the immunoprotection not only allows the use of allogeneic (same species) but also xenogeneic (different species) cell, which would solve the problem of donor scarcity.

Methods and Materials

Islets of Langerhans

The Islets of Langerhans are harvested by injection of a collagenase solution retrograde through the common bile duct into the pancreatic duct. The pancrease is excised, kept on ice and then digested at 37° C. The islets are separated from the rest of the pancreatic tissue using a filter device and a gradient centrifugation. The number of islets is counted under the microscope.

The islets are seeded onto a biodegradable polymer, either poly(glycolic acid) (PGA), or poly(L-lactic acid) and allowed to attach to the polymer.

Chondrocytes:

Cartilage tissue is harvested and digested using a collagenase solution. The cells are filtered and centrifuged to select the viable cells. Next the chondrocytes are plated on a culture dish and kept in culture using the appropriate culture medium until they form a confluent monolayer. The layer of cells is then detached from the bottom of the dish using a cell scraping device.

Covering of the islets on polymer with a monolayer of chondrocytes:

As shown schematically in FIG. 1, the detached layer of chondrocytes 10 is spread out as a flat layer. The islet loaded polymer 12 is laid onto the chondrocyte layer 10. The islet loaded polymer 12 is then completely wrapped with a chondrocyte layer 10, which is lifted up from the bottom of the dish.

Assessment of function of the device

The function of the device can be measured using several techniques. For example, the insulin content of the culture medium can be measured with a Radioimmuno-Assay (RIA) for insculture medium meaulin content of the culture medium measured with RIA after stimulation with glucose.

Histology (light and electron microscopy) can be used to assess the integrity of the chondrocyte layer and the insulin production of the islets. In vitro exposure of the chondrocytes/islets constructs to cellular and humoral components of the immunosystem can be used to demonstrate the immunoprotection of the chondrocyte matrix.

In vivo survival of the islet in immunocompetent animals and in treating diabetic animals can also be used to asses the efficacy of the device.

Figure 2:
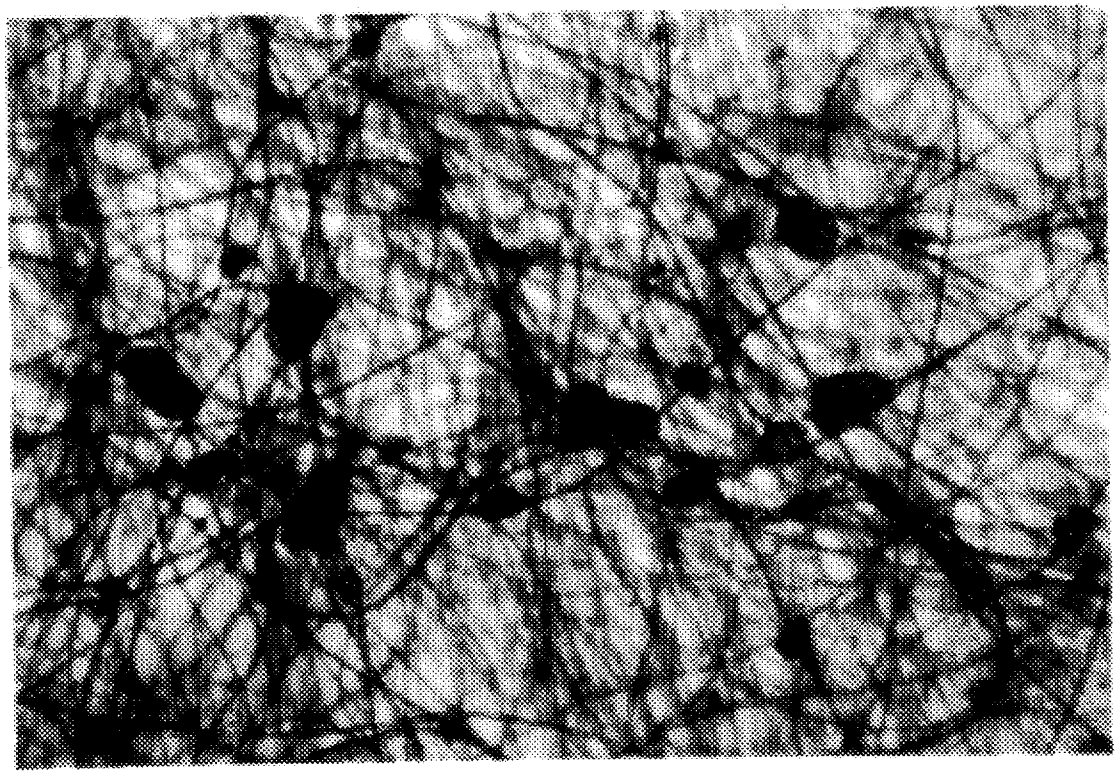
FIG. 2 is a micrograph (50×) of rat Islets of Langerhans on polyglycolic acid (PGA) fibers in culture for two weeks.
Figure 3:
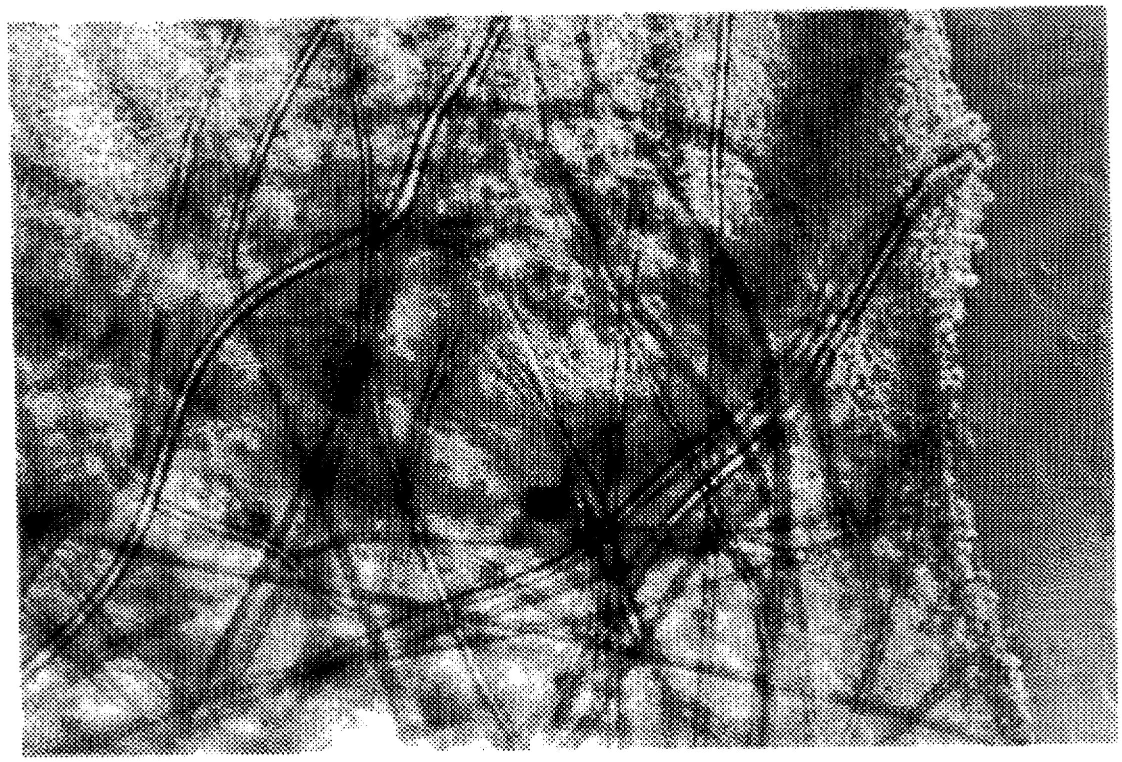
FIG. 3 is a micrograph (100×) of rat Islets of Langerhans on PGA polymer fibers in culture for nine days, wrapped with a monolayer of bovine chondrocytes for four days, showing the margin of the construct.

FIG. 2 is a micrograph of rat Islets of Langerhans on polyglycolic acid (PGA) fibers in culture for two weeks. FIG. 3 is a micrograph of rat Islets of Langerhans on PGA polymer fibers in culture for nine days, wrapped with a monolayer of bovine chondrocytes for four days, showing the margin of the construct. The islets are clumps of hundreds of cells. These are readily apparent in FIG. 2 and FIG. 3, even through the monolayer of cartilage forming the barrier.

Modifications and variations of the methods and materials described herein will be obvious to those skilled in the art from the foregoing detailed description. Such modifications and variations are intended to come within the scope of the appended claims.

I claim:

1. A method for immunoprotecting parenchymal cells for implantation comprising packaging the cells to be implanted completely within a barrier of immunoprotective tissue selected from the group consisting of cartilage, interior of the eye containing the vitreous humor, vascular endothelium of the brain, and maternal-fetal interface in the placenta, wherein the barrier is effective to immunoprotect the cells packaged therein and allows sufficient exchange of nutrients and gases to the packaged cells to maintain the viability of the cells.

2. The method of claim 1 wherein the immunoprotective tissue is cartilage and the cells are chondrocytes.

3. The method of claim 1 wherein the packaged cells are dissociated cells seeded onto a polymeric fibrous matrix.

4. The method of claim 1 wherein the barrier is formed by seeding dissociated cells onto a polymeric fibrous matrix.

5. The method of claim 4 wherein the barrier comprises a matrix formed of a biodegradable material.

6. Cells for implantation comprising parenchymal cells to be implanted completely packaged within a barrier of immunoprotective tissue selected from the group consisting of cartilage, interior of the eye containing the vitreous humor, vascular endothelium of the brain, and maternal-fetal interface in the placenta, wherein the barrier is effective to immunoprotect the cells packaged therein and allows sufficient exchange of nutrients and gases to the packaged cells to maintain the viability of the cells.

7. The cells of claim 6 wherein the immmunoprotective tissue is cartilage and the cells are chondrocytes.

8. The cells of claim 6 wherein the packaged cells are dissociated cells seeded onto a polymeric fibrous matrix.

9.The cells of claim 6 wherein the barrier is formed by seeding dissociated cells onto a polymeric fibrous matrix.

10. The cells of claim 9 wherein the barrier comprises a matrix formed of a biodegradable material.

* * * * *